(12) United States Patent
Pickhard

(10) Patent No.: US 8,728,042 B2
(45) Date of Patent: May 20, 2014

(54) INJECTION SYRINGE

(75) Inventor: Brigitte Pickhard, Grossebersdorf (AT)

(73) Assignee: Pharma Consult GES.m.b.H., Vienna (AT)

( * ) Notice: Subject to any disclaimer, the term of this patent is extended or adjusted under 35 U.S.C. 154(b) by 410 days.

(21) Appl. No.: 12/866,345

(22) PCT Filed: Jan. 19, 2009

(86) PCT No.: PCT/AT2009/000014
§ 371 (c)(1),
(2), (4) Date: Nov. 8, 2010

(87) PCT Pub. No.: WO2009/097634
PCT Pub. Date: Aug. 13, 2009

(65) Prior Publication Data
US 2011/0046561 A1    Feb. 24, 2011

(30) Foreign Application Priority Data
Feb. 7, 2008 (AT) .................................. A 203/2008

(51) Int. Cl.
*A61M 5/24* (2006.01)
*A61M 5/28* (2006.01)
*A61M 5/00* (2006.01)
*A61M 5/32* (2006.01)
*A61M 5/315* (2006.01)

(52) U.S. Cl.
USPC ........... 604/206; 604/110; 604/181; 604/187; 604/190; 604/192; 604/198; 604/200; 604/201; 604/218; 604/244

(58) Field of Classification Search
USPC ......... 604/110, 190, 192, 193, 198, 200, 201, 604/206, 228, 244, 263, 181, 187, 188, 197, 604/218, 240, 241, 242, 243
See application file for complete search history.

(56) References Cited

U.S. PATENT DOCUMENTS 3,820,652 A * 6/1974 Thackston ..................... 206/365
4,043,335 A * 8/1977 Ishikawa ....................... 604/190
(Continued)

FOREIGN PATENT DOCUMENTS

DE    29 821 609 U1    1/1999
EP    1 093 784 A2    4/2001
(Continued)

OTHER PUBLICATIONS

European Patent Office, Patent Translate, WO 03057289 English Translation of Description.*

(Continued)

*Primary Examiner* — Kevin C Sirmons
*Assistant Examiner* — Shefali Patel
(74) *Attorney, Agent, or Firm* — Ladas & Parry LLP

(57) ABSTRACT

An injection syringe, having a syringe cylinder, a plunger rod inserted therein and connected to a stopper by way of a coupling part, and a module that is provided in the proximal end of the syringe cylinder and having a cannula, mounted in a cannula holder received in a guided sleeve, and a sealing insert for the fluid-tight closure of the proximal end of the syringe cylinder and a protection cap for protecting the cannula, wherein the protective cap on the inner circumference has ribs extending in an axial direction, which engage in corresponding grooves of the driving part for a rotary drive thereof, and wherein in the sealing insert a hollow space is formed, which is closed on the proximal side and on the distal side transitions into an opening, by way of which a tip of the coupling part can be coupled to the hollow space.

11 Claims, 6 Drawing Sheets

(56) References Cited

U.S. PATENT DOCUMENTS

| | | | |
|---|---|---|---|
| 5,078,698 A | 1/1992 | Stiehl et al. | |
| 5,250,037 A | 10/1993 | Bitdinger | |
| 5,256,151 A | 10/1993 | Chul | |
| 6,059,756 A | 5/2000 | Yeh | |
| 6,613,016 B1 | 9/2003 | Ku | |
| 7,303,550 B2 | 12/2007 | Shue et al. | |
| 2003/0060775 A1 | 3/2003 | Shyu | |
| 2005/0277880 A1 | 12/2005 | Shue et al. | |

FOREIGN PATENT DOCUMENTS

| | | |
|---|---|---|
| EP | 1 514 566 A1 | 3/2005 |
| EP | 1514566 A1 * | 3/2005 |
| EP | 1 716 881 A1 | 11/2006 |
| GB | 1 517 447 | 7/1978 |
| WO | 91/00092 A1 | 1/1991 |
| WO | 96/03171 A1 | 2/1996 |
| WO | 97/49444 A1 | 12/1997 |
| WO | 03/057289 A1 | 7/2003 |
| WO | WO 03057289 A1 * | 7/2003 |
| WO | 2004/103431 A2 | 12/2004 |
| WO | 2005/037351 A1 | 4/2005 |
| WO | 2007/112470 A1 | 10/2007 |

OTHER PUBLICATIONS

International Search Report: PCT/AT2009/000014.

* cited by examiner

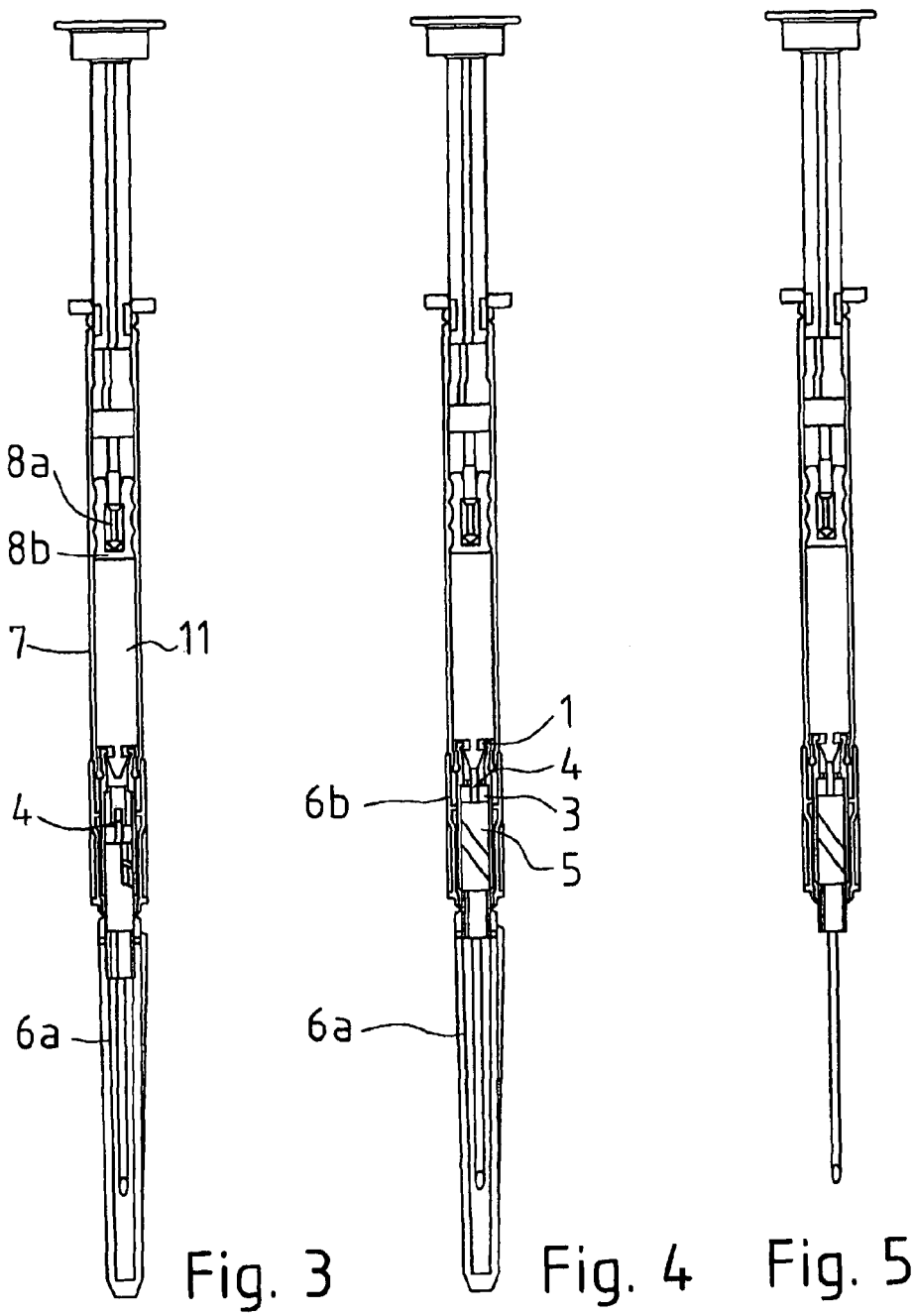

INJECTION SYRINGE

CROSS-REFERENCE TO RELATED APPLICATIONS

This is a 371 application of PCT/AT2009/000014, filed on Jan. 19, 2009, which claims foreign priority to A 203/2008 filed in Austria on Feb. 7, 2008. The entire declaration, oath, specification, disclosure, and drawing figures, and each of them, from said parent patent application are hereby incorporated herein by reference, thereto.

FIELD OF THE INVENTION

The invention relates to an injection syringe comprising a syringe cylinder, a plunger rod that is inserted therein and connected to a stopper by way of a coupling part, and a module that is provided in the proximal end of the syringe cylinder and comprises a cannula, which is mounted in a cannula holder received in a guiding sleeve, and further a sealing insert for the fluid-tight closure of the proximal end of the syringe cylinder and a protective cap for protecting the cannula, wherein the protective cap has on the inner circumference ribs extending in the axial direction, which engage in corresponding grooves of the guiding sleeve for a rotary drive thereof.

BACKGROUND

In the present description, the directions "proximal" and "distal" are defined as viewed from the side of the patient. An injection syringe with an originality closure, that is to say with a protective cap which can be removed only by rotating and connects the cannula to the syringe cylinder by the rotating, is known from WO 03/057289 AI. A disadvantage of this construction is that after the syringe has been used, the cannula is unprotected, which on the one hand means a risk of injury and on the other hand causes the unwanted dispersal of residues of the medicament out of the syringe cylinder. WO 2007/112470 AI discloses an injection syringe comprising a syringe head which can be displaced into the syringe cylinder. Immediately after the syringe has been used, the plunger rod couples to the syringe head and allows this to be drawn into the syringe cylinder. The disadvantage of this design is that the cannula, which is firmly connected to the syringe cylinder, is provided only with a conventional protective cap. Unintentional jolts on the plunger rod of the syringe before its use can lead to the medicament entering into the cannula and emerging from it in an uncontrolled manner.

Injection syringes are also known which either are provided with an originality closure or have syringe heads which can be guided into the syringe cylinder after the injection by withdrawing the plunger rod. A combination of the known constructions is not possible. WO 1997 49444 A and WO 1996 03171 disclose originality closures which are mounted on syringe cylinders which become slimmer at the proximal end both in outer circumference and on the inner circumference and thus form a channel for liquid.

DE 29 821 609 UI discloses an injection syringe comprising a syringe head which can be drawn into the syringe cylinder. Providing this head with a known originality closure cannot lead to a solution, because the syringe head insert with a cannula described there could be connected to the syringe cylinder neither in a manner stable to tilting nor in a rotation-proof manner and therefore could not ensure safe handling. WO 1991 00092 AI and EP 1 514 566 AI disclose means for coupling the plunger rod and syringe head with the cannula. These syringe heads do not have originality closures, because essential parts of them are made of a sealing material to which no parts of an originality closure can be connected. US 2005 0 277 880 AI and U.S. Pat. No. 5,256,151 disclose syringe heads which can be coupled, of which the means for holding the cannula are too complex to be supplemented with an originality closure. U.S. Pat. No. 5,078,698 discloses an injection syringe with retractable protective claws which release the cannula. Syringes of this type have the disadvantage that the cannula is permanently connected to the syringe cylinder and cannot be covered again sufficiently tightly by the claws after the injection.

SUMMARY OF THE INVENTION

The object of the present invention is to avoid the disadvantages of injection syringes without an originality closure and injection syringes without a syringe head which can be drawn into the syringe cylinder, and to provide an injection syringe of the type described in the introduction which both connects the cannula and the syringe cylinder to one another only on removal of the protective cap, and renders it possible to displace the syringe head together with the cannula into the cylinder after use. The invention is distinguished in that in the sealing insert a hollow space is formed, which is closed on the proximal side and on the distal side transitions into an opening, by way of which a tip of the coupling part can be coupled to the hollow space.

The sealing insert is constructed such that it both has a hollow space by way of which it can be coupled to the plunger rod and thus can be displaced into the syringe cylinder, and is closed by a wall on its proximal side. This wall ensures the sealing of the syringe cylinder until the injection syringe is used. To use the injection syringe, the wall is punctured with the distal end of the cannula, as a result of which the required connection between the volume of the syringe cylinder and the cannula is established. When the injection is completed, the cylinder stopper and the sealing insert couple to one another. On withdrawal of the cylinder stopper by way of the plunger rod, the sealing insert and the guiding sleeve firmly connected to it are moved into the syringe cylinder. The guiding sleeve thereby takes with it the module of cannula, cannula holder and driving part. By this construction, the injection syringe described requires fewer components and is therefore simpler to produce and safer to handle than an injection syringe which, for example according to U.S. Pat. No. 6,613,016 B1, is connected to an originality closure according to, for example, WO 1997 49444 A.

A preferred embodiment of the invention is distinguished in that the sealing insert is constructed at the proximal end of the syringe cylinder such that the guiding sleeve can be inserted firmly into the sealing insert, for example by way of a coaxial, annular coupling. Furthermore, in the sealing insert a hollow space is formed, which is open towards the inside of the syringe cylinder, so that the tip of the plunger rod can engage in the hollow space after the injection operation. The sealing insert is closed on the proximal side, the wall to the hollow space of the sealing insert being constructed as a membrane, so that on the one hand the inside of the syringe cylinder is closed tight, and on the other hand the pointed distal end of the cannula can puncture this membrane. The one-piece construction of the sealing insert with these properties renders possible a short design of the syringe head and is inexpensive and safe.

The cannula is held axially symmetrically by a cannula holder inserted in the guiding sleeve such that it can be displaced by sliding axially in a straight line. Before operation of the originality closure, by way of which the protective cap is rotated and the cannula holder together with the cannula is moved in the direction of the sealing insert, the distal end of the cannula ends before this sealing insert. In order to puncture the membrane of the sealing insert during this operation, the distal end of the cannula is sharpened by way of an angled cut, for example by a method with anticoring.

In an alternative embodiment, a filter attachment and a filter between the cannula and the filter attachment are arranged at the distal end of the cannula, the filter being held over the opening of the cannula and/or the opening of the cannula holder by way of the filter attachment. The distal side of the filter attachment has an angled cut in order to puncture the sealing insert.

It advantageous if the outer circumference of the guiding sleeve is equal to the inner circumference of the proximal end of the syringe cylinder or the inner circumference of the distal end of the protective cap or both, since the guiding sleeve is then held axially symmetrically in a tilt-proof manner.

The essentially tubular protective cap has a radial predetermined breaking point which breaks when the protective cap is rotated, so that the outer section of the protective cap can be removed and the inner section remains firmly connected to the syringe cylinder. The firm connection of the distal section of the protective cap to the syringe cylinder is rendered possible by this section being pushed over a substantial part of its length over the syringe cylinder and, for example, lying against it with a positive fit and/or being latched by way of a corresponding annular bead on the syringe cylinder.

In order to connect the syringe cylinder quickly and easily to the protective cap in the production process and at the same time to effect a tight connection between the two, the distal section of the protective cap has an annular grove on the inside, in which a sealing ring is arranged.

In order to be able to withdraw the cannula completely into the syringe cylinder after the injection operation, the module of the of the injection head, minus the dimension from the proximal end of the syringe cylinder to the distal front face of the sealing insert, is, in the axial direction, shorter than or equal to the stroke of the plunger rod.

So that the tip of the coupling part can be inserted into the cylinder stopper and can puncture it during operation of the syringe, the cylinder stopper has a pocket hole, the base of which is thin.

Since the coupling part is to release the plunger rod after the module of the syringe head has been withdrawn into the syringe cylinder, the distal end of the coupling part transitions into holding claws, in which the plunger rod can be engaged and uncoupled by way of a coupling head.

The syringe cylinder has at the distal end an annular bead on the inside, so that the coupling part strikes against this when the plunger rod is withdrawn, and when pulled further the plunger rod uncouples from the coupling part.

For final closing of the syringe cylinder with the cannula inside, the distal end of the plunger rod is constructed as an end sleeve, the internal diameter of which corresponds to the external diameter of the proximal end of the section of the protective cap firmly connected to the syringe cylinder. In this manner, the uncoupled plunger rod serves as a plug for the syringe cylinder.

BRIEF DESCRIPTION OF THE DRAWING

The invention is explained in more detail in the following with the aid of an example shown in the drawings. In these:

FIG. 3 shows a longitudinal section through the entire syringe before use, FIG. 4 shows a longitudinal section through the entire syringe after connection of the cannula to the syringe cylinder, FIG. 5 shows a longitudinal section through the entire syringe after removal of the protective cap.

DETAILED DESCRIPTION OF THE DRAWING

Figure 1:
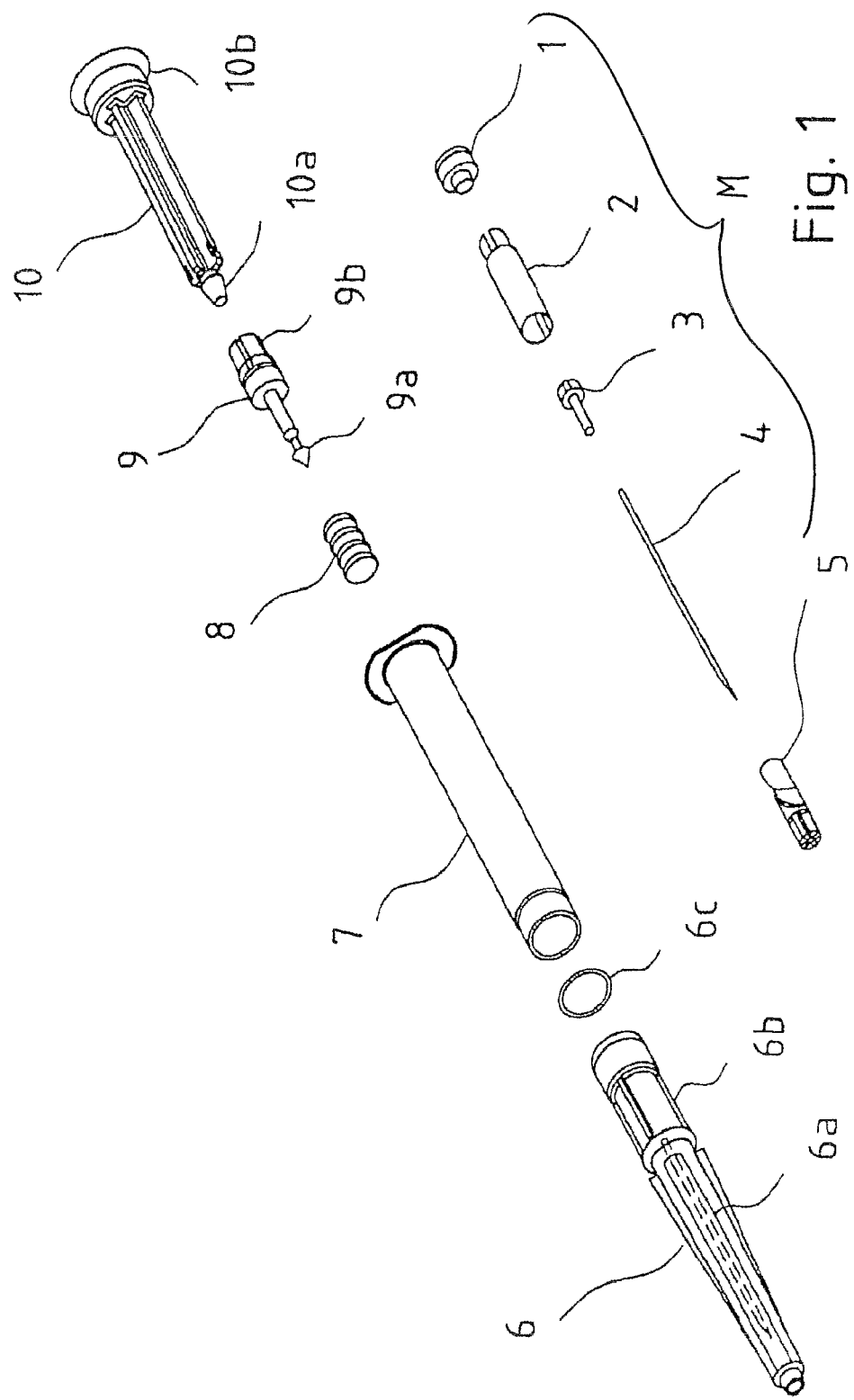
FIG. 1 shows an illustration of the individual parts of the injection syringe.

According to FIG. 1, the injection syringe has a syringe cylinder 7, on the proximal end of which is arranged a module (M) of a sealing insert 1, a guiding sleeve 2 firmly connected to this and with cannula holder 3 arranged therein such that it can be displaced by sliding, cannula 4 and driving part 5 which can be displaced by rotating. The proximal end of the assembled syringe is closed with a protective cap 6 mounted on the syringe cylinder 7 such that it provides a seal by way of a sealing ring 6c. At the distal end of the syringe cylinder 7 is arranged a module (M) of a cylinder stopper 8 and coupling part 9 inserted therein and plunger rod 10.

FIG. 3 shows the assembled and drawn out syringe, which contains a liquid medicament 11 in the syringe cylinder 7. The protective cap 6 has not yet moved and the cannula 4 is not yet connected to the syringe cylinder. The coupling part 9 is inserted into a pocket hole 8a which has a base 8b.

Figure 6:
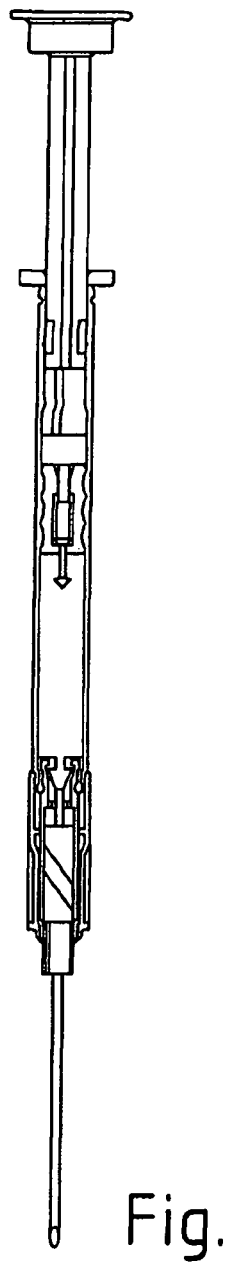
FIG. 6 shows a longitudinal section through the entire syringe with the cylinder stopper punctured.

In FIG. 4, a proximal section 6a of the protective cap 6 is rotated, as a result of which its connection to a distal section 6b of the protective cap is broken, and the cannula 4 is moved in a straight line by way of the cannula holder 3 and the driving part 5 towards the sealing insert 1 and punctures this without generating particles. After removal of the proximal section 6a of the protective cap 6, as shown in FIG. 5, the injection syringe is ready for use. According to FIG. 6, when the plunger rod 10 is pressed on, the tip 9a of the coupling part 9 punctures the base 8a of the cylinder stopper 8, again without generating particles. The cylinder stopper 8 then moves in the direction of the sealing insert 1, as a result of which the medicament emerges from the injection syringe through the cannula 4.

Figure 2:
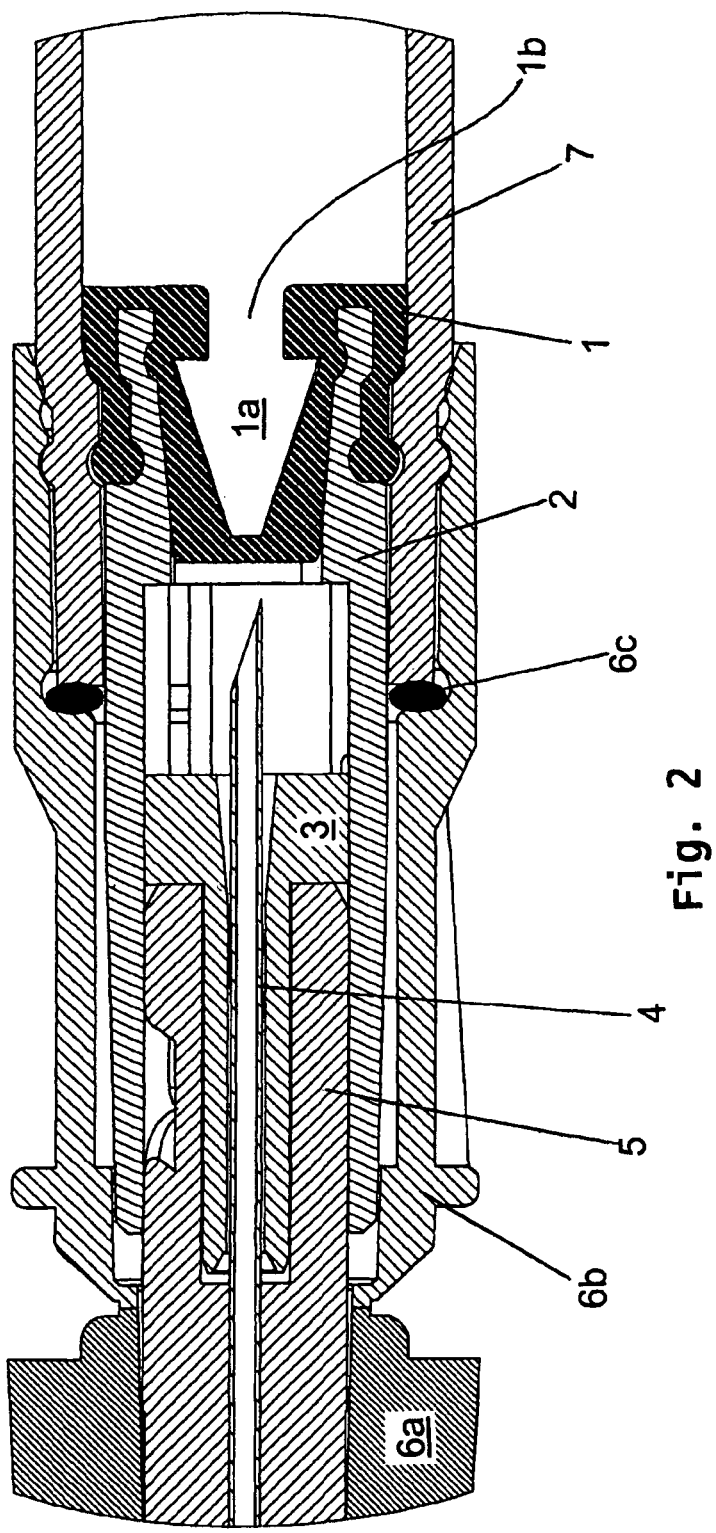
FIG. 2 shows a longitudinal section through the syringe head.
Figure 7:
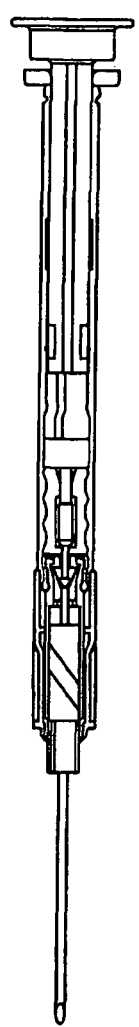
FIG. 7 shows a longitudinal section through the entire syringe after the injection.

FIG. 7 shows the injection syringe after the injection. The cylinder stopper 8 is mounted on the sealing insert 1, and the tip 9a of the coupling part 9 engages in the sealing insert 1. FIG. 2 shows that, for this purpose, the sealing insert has a hollow space 1a, which has on its distal end an opening 1b, the diameter of which is smaller than the diameter of the hollow space 1a.

Figures 8, 9:
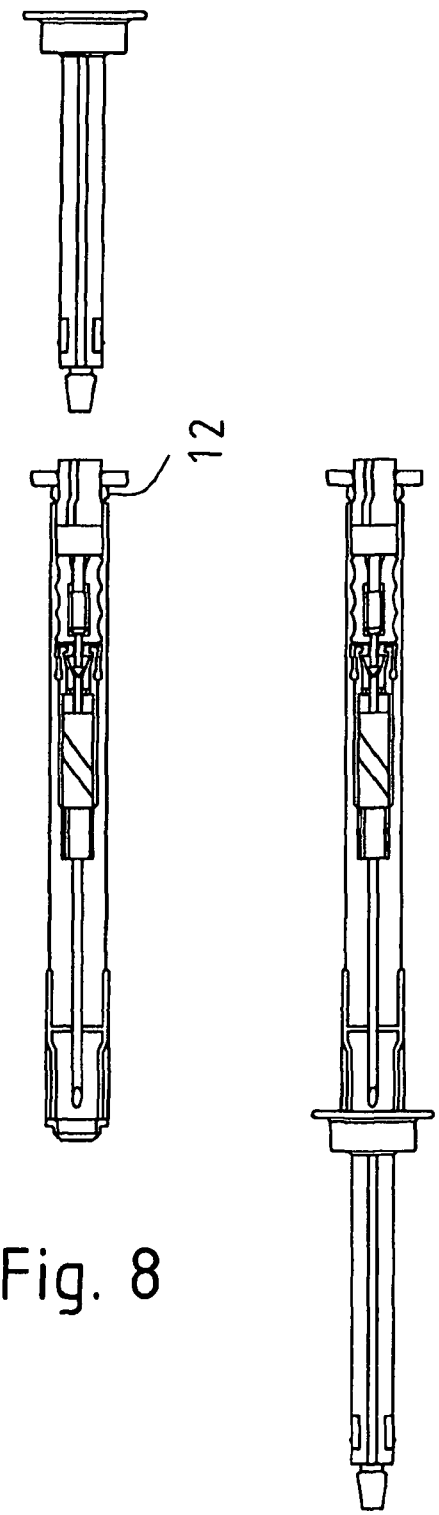
FIG. 8 shows a longitudinal section through the entire syringe after drawing in the cannula.
FIG. 9 shows a longitudinal section through the entire syringe after closing the syringe cylinder.

FIG. 8 shows how the module of the syringe head is drawn into the syringe cylinder 7. The plunger rod 10 is pulled and the coupling part 9, together with the sealing insert 1 and the guiding sleeve 2 firmly connected to this, moves into the chamber of the syringe cylinder 7. As a result, the cannula holder 3 with the cannula 4 and the driving part 5 are also guided into the syringe cylinder 7. The connection between the sealing insert 1 and guiding sleeve 2 is achieved, as shown in FIG. 2, by the two being inserted into one another and firmly coupled in by way of a coaxial annular groove. FIG. 8 furthermore shows that the coupling part 9 is mounted on an annular bead 12 during withdrawal, so that, when pulled further, the plunger rod 10 uncouples from the coupling part 9.

FIG. 9 shows that the plunger rod 10 can be mounted on the proximal opening of the syringe cylinder 7, which is formed, for example, by the distal section 6b of the protective cap 6, and closes this.

Figure 10:
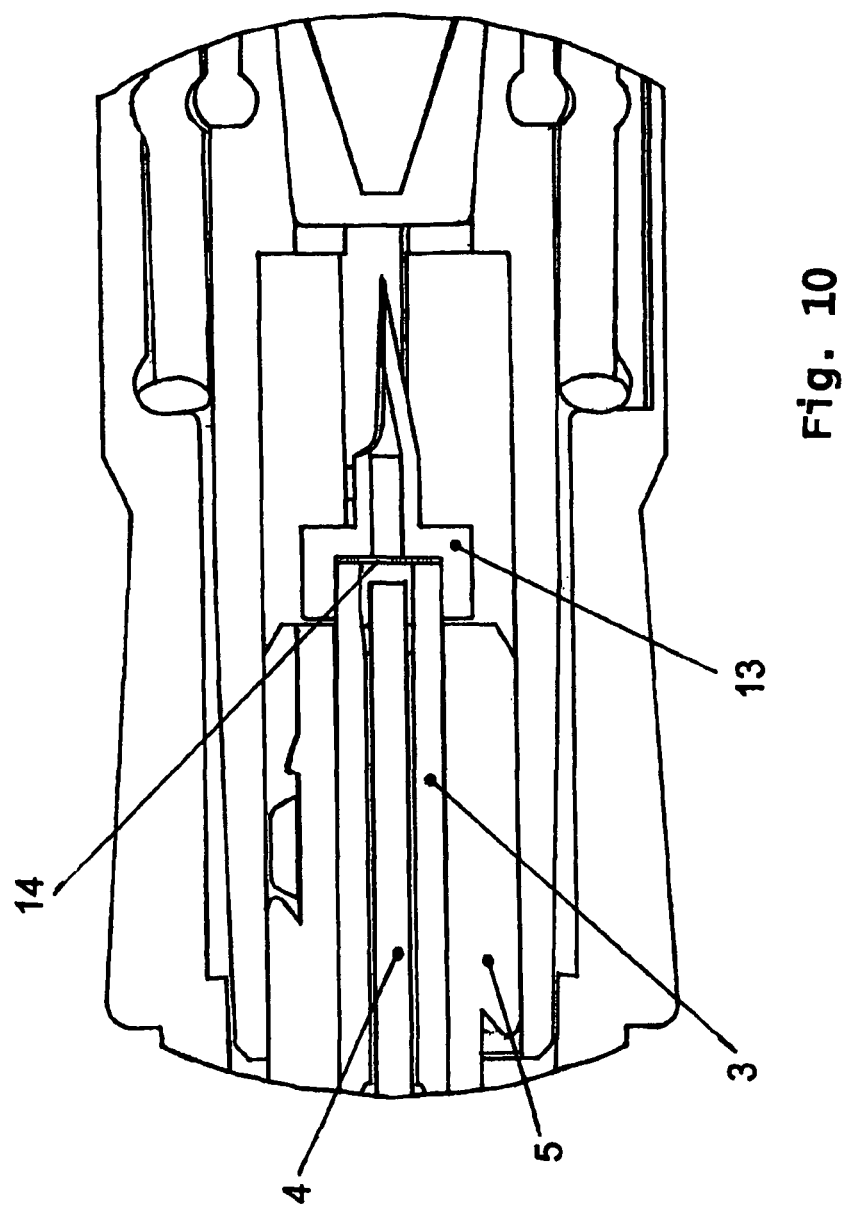
FIG. 10 shows a longitudinal section through the syringe head.

According to FIG. 10, in an alternative embodiment the distal end of the cannula 4 can have a straight cut instead of an angled cut, the tip which punctures the sealing insert 1 being provided by a filter attachment 13 which holds a filter 14 at the distal end of the module of cannula 4 and cannula holder 3. This alternative embodiment has the advantage of having a particle filter downstream of all components where particles can enter into the medicament during preparation and during the injection.

The invention claimed is:

1. An injection syringe comprising a syringe cylinder, a plunger rod that is inserted therein and connected to a stopper by way of a coupling part, and a module (M) that is provided in a proximal end of the syringe cylinder and comprises a cannula, which is mounted in a cannula holder received together with a driving part, which is drivable by the cannula holder, in a guiding sleeve, and further a sealing insert for a fluid-tight closure of the proximal end of the syringe cylinder and a protective cap for protecting the cannula, wherein the protective cap has on an inner circumference ribs extending in an axial direction, which engage in corresponding grooves of the driving part for a rotary drive thereof, wherein in the sealing insert a hollow space is formed, which is closed on a proximal side and on a distal side transitions into an opening, by way of which a tip of the coupling part can be coupled to the hollow space, wherein a proximal front face of the sealing insert and a distal front face of the guiding sleeve are constructed axially symmetrically and can be inserted firmly into one another: and wherein an outer circumference of the guiding sleeve is equal to an inner circumference of the proximal end of the syringe cylinder and to an inner circumference of a distal end of the protective cap, in order to hold the guiding sleeve axially symmetrically in a tilt-proof manner.

2. The injection syringe according to claim 1 wherein the cannula ends at a distal end of the cannula before a closed proximal side of the sealing insert, and in that the distal end of the cannula, as is known per se, has an angled cut.

3. The injection syringe according to claim 1 wherein a filter attachment is arranged at a distal end of the cannula, a filter being provided between the cannula and filter attachment and being held by the filter attachment over an opening of the cannula and/or an opening of the cannula holder, and in that a distal side of the filter attachment has an angled cut.

4. The injection syringe according to claim 1 wherein the protective cap, as is known per se, is formed by two essentially tubular sections lying one after the other, which are connected to one another by way of a predetermined breaking point.

5. The injection syringe according to claim 4, wherein a distal section of the protective cap is pushed along a substantial part of a length of the distal section of the protective cap over the proximal end of the syringe cylinder, as is known per se, is firmly connected to the proximal end of the syringe cylinder.

6. The injection syringe according to claim 4 wherein a distal section of the protective cap has an annular groove on an inside, in which a sealing ring is arranged by way of which a tight connection can be established between the distal section of the protective cap and proximal end of the syringe cylinder.

7. The injection syringe according to claim 1 wherein the module (M) of the cannula, cannula holder, driving part, guiding sleeve and sealing insert inserted into one another, minus a dimension from the proximal end of the syringe cylinder to a distal front face of the sealing insert, is shorter than or equal to a stroke of the plunger rod in the axial direction.

8. The injection syringe according to claim 1 wherein the coupling part, as is known per se, is inserted by means of the tip into the stopper, the stopper having a corresponding pocket hole, a base of which can be punctured by the tip.

9. The injection syringe according to claim 1 wherein the coupling part transitions at a distal end, as is known per se, into holding claws, in which a coupling head of the plunger rod is engaged.

10. The injection syringe according to claim 1 wherein the syringe cylinder, as is known per se, has an annular bead on an inside.

11. The injection syringe according to claim 1 wherein a distal end of the plunger rod, as is known per se, has an end sleeve, an internal diameter of which corresponds to an external diameter of a proximal end of a section of the protective cap firmly connected to the syringe cylinder.

* * * * *